(12) United States Patent
Steinrisser et al.

(10) Patent No.: US 8,312,757 B2
(45) Date of Patent: Nov. 20, 2012

(54) METHOD AND SAMPLE FOR TESTING A MEASURING INSTRUMENT FOR GRAVIMETRIC MOISTURE DETERMINATION

(75) Inventors: Markus Steinrisser, Männedorf (CH); Helen Vogt, Zürich (CH); Claas Boerger, Zürich (CH); Dominik Gössi, Benglen (CH)

(73) Assignee: Mettler-Toledo AG, Greifensee (CH)

( * ) Notice: Subject to any disclaimer, the term of this patent is extended or adjusted under 35 U.S.C. 154(b) by 0 days.

(21) Appl. No.: 13/270,086

(22) Filed: Oct. 10, 2011

(65) Prior Publication Data

US 2012/0060593 A1     Mar. 15, 2012

Related U.S. Application Data

(63) Continuation of application No. PCT/EP2010/054985, filed on Apr. 15, 2010.

(30) Foreign Application Priority Data

Apr. 16, 2009 (EP) .................................... 09158085

(51) Int. Cl.
    *G01N 21/00* (2006.01)
(52) U.S. Cl. ......................................... 73/1.02
(58) Field of Classification Search .................. None
    See application file for complete search history.

(56) References Cited

U.S. PATENT DOCUMENTS

| 5,085,527 A | 2/1992 | Gilbert |
| 5,485,684 A | 1/1996 | Philipp et al. |
| 5,983,711 A * | 11/1999 | Pappas et al. .................... 73/76 |
| 6,331,683 B1 | 12/2001 | Spannagel et al. |
| 6,462,321 B2 | 10/2002 | Revesz et al. |
| 6,566,637 B1 | 5/2003 | Revesz et al. |
| 7,148,455 B2 | 12/2006 | Scalese et al. |
| 7,617,717 B2 | 11/2009 | Lüchinger |

FOREIGN PATENT DOCUMENTS

WO     99/61878 A2     12/1999

* cited by examiner

*Primary Examiner* — Robert R Raevis
(74) *Attorney, Agent, or Firm* — Standley Law Group LLP

(57) ABSTRACT

A predetermined test sample is used to test a measuring instrument (10) for gravimetric moisture determination. The measuring instrument has a test chamber (30), a weighing device (40) for determining the mass of a sample contained in a sample holder (60) in a measuring position in the test chamber, and at least one means for heating (31) the sample on the sample holder. The test sample is placed on the sample holder and its initial mass is determined. The test chamber is heated, using a predefined temperature profile. After heating, the subsequent mass of the test sample is determined, using the weighing device. By comparing this subsequent mass to a reference mass for the test sample, a signal corresponding to the result of the comparison is generated and transmitted.

17 Claims, 3 Drawing Sheets

METHOD AND SAMPLE FOR TESTING A MEASURING INSTRUMENT FOR GRAVIMETRIC MOISTURE DETERMINATION

CROSS-REFERENCE TO RELATED APPLICATIONS

This application is a continuation under 35 USC §120 of PCT/EP2010/054985, filed 15 Apr. 2010, which is in turn entitled to benefit of a right of priority under 35 USC §119 from European patent application 09 15 8085.2, which was filed on 16 Apr. 2009. The content of each of the applications is incorporated by reference as if fully recited herein.

TECHNICAL FIELD

The present invention relates to a method for testing a measuring instrument for gravimetric moisture determination and a test sample suitable for this purpose. In this context, moisture is understood to mean the presence of thermally volatile substances, such as water or other liquids, in another substance.

BACKGROUND OF THE ART

To determine the moisture content of a sample, the sample is dried and its weight is determined before and after the drying process.

Under certain circumstances, the weight loss may also be measured during the drying process. In this case, the weight value for a sample decreases as a function of the temperature, the drying time, and the conditions in the test chamber, wherein the weight value follows a weight-time curve that asymptotically approaches the dry weight of the sample. In order to test whether the moisture of a sample is equivalent to a predefined nominal value, the weight-time curve of the sample is calculated. Then, the weight-time curve calculated in this manner is compared with a comparison curve that is determined in comparison experiments. The comparison curve is based on a weight-time curve that has been obtained using a sample whose moisture is equivalent to the nominal value. If the calculated weight-time curve and the comparison curve do not match within predefined tolerances, the moisture of the sample is equivalent to the nominal value within the predefined tolerance value.

An appropriately equipped measuring instrument for gravimetric moisture determination is able to measure the moisture content of a sample on the basis of the measured curve parameters and the drying time, and to display such values on a display unit using existing electronic means, which include associated computing and storage capability. With this method, the material to be dried no longer has to be completely dried out, it is sufficient to determine the coordinates of two detection points in the weight-time diagram.

The drying process in which the material to be dried is not completely dried out may be conducted for a predefined, constant drying time $\Delta t$. Alternatively, the drying process may be continued until the change in mass per unit of time in falls below a predefined threshold value a during the drying process, wherein the drying time $\Delta t$ does not necessarily have to be constant.

As noted, the change in weight of a sample during the drying process depends essentially on the temperature, the drying time, and the conditions in the test chamber. A chamber that may be opened to allow the deposit or removal of a sample, and which is enclosed by the housing of the measuring instrument serves as the test chamber. An arrangement for holding the sample and a means for heating the sample are also located inside the test chamber. The sample holder is connected to a gravimetric measuring instrument.

Normally, a thin film of the sample is deposited on a flat sample holder, for example a sample tray. The tray is arranged in the measuring instrument for gravimetric moisture, preferably with its surface area horizontal and parallel with respect to the surface area of means for heating the sample, to enable the sample to be heated evenly.

Various radiation sources, such as radiant heaters, ceramic heaters, halogen lamps and quartz lamps are used as the heating means. It is even possible to use microwave generators as a source of radiant heat.

A measuring instrument for gravimetric moisture determination of the species described is known for example from European patent specification EP 0 611 956 B1. In this device the sample holder is loaded outside of the measuring instrument for gravimetric moisture determination. To do this, the weighing device is extracted from the measuring instrument housing together with the sample holder on a pull-out device in the form of a drawer. An annular halogen lamp is used as the radiation source, and is located above the sample holder when in operation.

Another measuring instrument is known from European patent application EP 1 850 110 A1. In this device, two radiation sources are used, and in the measurement position the sample holder is arranged between the first and the second radiation sources.

To assure that the measuring instrument for gravimetric moisture determination is functioning precisely, it must be tested regularly, and adjusted or calibrated as necessary. One option is to test the weighing device and the radiation source separately from one another. In order to test the weighing device, a known reference mass can be placed on the mass sensor. If the mass displayed by the measuring instrument differs excessively from the reference mass, the mass sensor must be readjusted. In order to test the radiation source, a reference temperature sensor can be inserted in the measuring instrument instead of the sample. The measuring instrument is then heated to a predefined reference temperature. If the temperature displayed by the measuring instrument differs excessively from the reference temperature, the radiation source must be readjusted. Reference temperature sensors are known for example from German patent DE 100 24 015 C2.

Testing of the radiation source is particularly time-intensive, since the reference temperature sensor must be inserted in the cold measuring instrument in order to obtain the best accuracy possible. In this context, the measuring instrument is understood to be cold if it is at room temperature, approximately 20° C. It is also necessary to wait until the instrument has reached a stable state and the reference temperature sensor does not display any temperature fluctuations, and this too takes a great deal of time. In order to ensure that the radiation source is absolutely reliable, it is further recommended to carry out this test for more than just one reference temperature. As a consequence, the test requires significant effort, and is therefore often performed irregularly by the user, which in the meantime may also lead to uncertainties regarding measurement accuracy.

A test of the reproducibility of measurement results is described in published application US 2002/063128 A1. For this test, milk powder from five different manufacturers is used. Two samples of the milk powder from each manufacturer are taken, and the moisture content in each of these samples is determined. The measurement results for two corresponding samples may be compared. Conclusions regarding the reproducibility of the measurement results may be drawn on the basis of these measurements. However, no conclusions can be drawn regarding the absolute accuracy of the procedure. If the measurement device were to show an incorrect value, this would lead to a systematic error. The measured values recorded with the faulty measurement device would be the same.

In another analysis method, which is also lengthy, however, the moisture of a test substance is determined using a Karl Fischer titration procedure. Then, a comparison sample is taken from the test substance and the moisture of the comparison sample is determined using the measuring instrument. If the measuring instrument returns a sufficiently accurate result, within the parameters of permissible error tolerances, the measuring instrument does not need to be adjusted or calibrated again. However, if the result is outside the permissible error tolerances, the measuring instrument must be adjusted and/or calibrated.

The drawback of this analysis method too is that determining the moisture of the test substance by Karl Fischer titration is a lengthy process and consequently is often carried out only sporadically by the user, and here too this can lead to uncertainties regarding the accuracy of the measurement.

WO 99/61878 A and US 2002/063128 A1 disclose other analysis methods, which are also time consuming. In these methods, the moisture of a test substance is determined using a standard convection oven. For this purpose, a sample of the liquid-containing test substance is first weighed, and then dried in the convection oven. After drying, the sample is weighed again. The moisture content of the test substance can be determined from the weight difference of the sample before and after it is dried. This analysis method also suffers from the drawback that determining the moisture of the test substance is time consuming and therefore is often not carried out regularly by the user.

The object, then, is to provide a method for testing a measuring instrument for gravimetric moisture determination, and a suitable test sample therefore, enabling the measuring instrument to be tested as simply and accurately as possible.

SUMMARY

This object is solved with a method and a suitable test sample therefore, having the features described in the independent claims. Other advantageous embodiments may be discerned from the subordinate claims.

A disclosed embodiment of a method according for testing a measuring instrument for gravimetric moisture determination, wherein the measuring instrument has a test chamber, a weighing device with a sample holder for determining the mass of the sample, which is located in the test chamber when in the measurement position, and at least one means for heating the sample that is placeable on the sample holder, comprises the following steps:

Placing a test sample on the sample holder;
Determining starting mass $m_0$ of the test sample;
Heating test chamber using a predefined temperature profile;
Measuring mass $m_1$ of the test sample using the weighing device after the test sample has been heated according to the predefined temperature profile;
Comparing measured mass $m_1$ to a reference value of mass $m_*$; and
Outputting a signal corresponding to the result of a comparison.

In this context, starting mass $m_0$ of the test sample and mass $m_1$ after the test chamber has been heated according to the predefined temperature profile may be determined via the weighing device of the measuring instrument. Alternatively, starting mass $m_0$ may also be determined in some other way. For example, starting mass $m_0$ may be determined using a scale outside the measuring instrument for determining moisture, and the mass determined in this way may either be transmitted to the measuring instrument electronically or input by the user.

The purpose of the test sample is to test the measuring instrument. For this to be possible, the test sample must have known properties. These known properties may include for example a known starting mass $m_0$ and/or a mass $m(t,T)$ that is dependent on the temperature profile. From these known properties, it is possible to derive a reference value that may be used for testing the measuring instrument. One possible reference value is the mass $m_*$ that is present after the test sample has been heated according to a predefined temperature profile.

For example, in order to determine the reference value of mass $m_*$, a sample of a given substance with known starting mass $m_0$ may be placed in a measuring instrument for gravimetric moisture determination, where it is heated according to a predefined temperature profile. The mass that remains after heating corresponds to reference mass $m_*$. It must be ensured before determining the reference mass that the function of the measuring instrument being used is accurate. A sample may be used to test the measuring instrument. Reference mass $m_*$ does not need to be determined before each test. Ideally, the substance is stable for a prolonged period, that is to say heating the sample according to a predefined temperature profile should always result in the same reference mass $m_*$ even after the substance has been kept in storage.

In one possible use, test samples are packed in such manner that they return a reproducible reference mass $m_*$ even after they have been stored for an extended period and subsequently undergone the method for testing the measuring instrument.

Percentage changes in mass may also be considered instead of absolute masses $m_0$, $m_1$ and $m_*$. For this purpose, for example, the masses under consideration may be normalised with starting mass $m_0$. Another possible parameter is the relative change in moisture X, which may be derived directly from the change in mass. The predefined temperature profile preferably includes heating the test chamber to a predefined target temperature $T_1$ and maintaining this target temperature $T_1$ either for a predefined time interval $\Delta t$ or until the change in mass per unit of time M falls below a predefined value a, that is to say when in $\dot{m} \leq a$.

However, it is also possible to use a different temperature profile for heating the test chamber. Target temperature $T_1$ must also be high enough to effect a sufficiently large change in mass. The target temperature is typically selected to be above 100° C.

The output of a signal corresponding to the result of the comparison may be an alarm signal, for example, which is output if the difference between the reference value of mass $m_*$ and the measured mass $m_1$ is greater than a predefined tolerance. Such an alarm signal is understood to be for example a visual display, a printout on paper, an acoustic signal, or an electronic signal that is transmitted to another instrument.

Instead of outputting an alarm signal, measured mass $m_1$ may also be read off by the user and compared with reference value $m_*$. However, the disadvantage of this manual comparison is that it requires more effort on the part of the user and is more susceptible to error.

In a preferred embodiment, an information carrier may be assigned to the test sample, and the data stored on such carrier may be transmittable to the measuring instrument. The stored data may include for example starting mass $m_0$ and/or a reference value of the mass, such as $m_*$. This data may also include mass profile $m(t,T)$ as it is determined by the temperature profile. In this context, barcodes, matrix code, microchips, radio frequency identification (RFID) tags and the like may be used as information carriers.

The advantage of the disclosed is that it not only enables the mass sensor and the means for heating to be tested at the same time. It is possible to draw a conclusion regarding the accuracy of the entire test setup. For example, experiments have shown that even small changes in the test chamber, such as the air circulation in the test chamber, may have a significant effect on the measurement result. Such changes are also recorded by the disclosed method in that a distinction occurs between measured mass $m_1$ and the reference value of mass $m_*$.

The disclosed method has the advantage that absolute values of the mass are compared. In this way, it is not merely the relative accuracy but the absolute accuracy of the measuring instrument that is tested.

Ideally, a test sample having known starting mass $m_0$ is used in the disclosed method. For example, a substance for which the measuring instrument for gravimetric moisture determination would normally be used anyway might be used as the test substance. One problem in this case is that the measuring instrument is used primarily for determining the moisture in substances that are changed by time and temperature fluctuations during storage. Typical applications are the determination of moisture in foodstuffs, for example milk powder, coffee, chocolate, cornstarch or flour. This substances are prone to undergo changes as a result of time and environmental influences. Therefore, it is not possible to create a comparison sample from such substances, store it for prolonged periods, and then use it for testing the measuring instrument. Even if these difficulties could be overcome, a further disadvantage of such substances is that the change in mass they undergo as a result of applying the temperature profile is too small, and therefore does not allow a sufficiently accurate conclusion to be drawn regarding the accuracy of the measuring instrument.

The test substance should preferably be chemically and physically stable when stored under normal conditions for a prolonged period, so that it is possible to store the test substance. A test substance that is used and recommended for testing measuring instruments is sodium tartrate dihydrate, a salt having bonded water of crystallisation which is split off under the effect of heat. The separation of the water of crystallisation is complete at a temperature threshold value $T_S$ of about 150° C. A target temperature that is higher than this temperature threshold value $T_S$ thus results in a practically unchanged mass. Therefore, sodium tartrate dihydrate is not suitable for performing a precise test of the measuring instrument above temperature threshold value $T_S$. Sodium tartrate dihydrate is also unsuitable for use below temperature threshold value $T_S$, since in this range it is not possible to reproduce the mass-temperature curve with sufficient accuracy, that is to say the curve is different for each sample. Therefore, sodium tartrate dihydrate is also unsuitable for performing a precise test of the measuring instrument below temperature threshold value $T_S$.

This problem may be circumvented by ensuring that the test substance contained in the test sample has a reproducible temperature-mass curve in a temperature about target temperature $T_1$. Natural substances such as milk powder, coffee, chocolate, cornstarch or flour are not suitable, since they do not have a reproducible temperature-mass curve.

In addition, the material of the test sample is selected such that the change in mass as effected by target temperature $T_1$ is sufficiently substantial to enable an associated reference value of mass $m_*(T_1)$ to be assigned unambiguously to target temperature $T_1$. In order to be able to guarantee this, the value $dm_*(T_1)/dT_1$ derived in a temperature range about target temperature $T_1$ from mass reference value $m_*(T_1)$ after target temperature $T_1$ is greater than the quotient of mass tolerance $G_m$ of the weighing device and temperature tolerance $G_T$ of target temperature $T_1$. Natural substances such as milk powder, coffee, chocolate, cornstarch or flour do not possess these properties. Typically for those substances, a relatively sharp mass reduction occurs in the early stage of heating, as volatile substances such as water evaporate. The gradient of this mass reduction does manifest a large change in mass relative to the rise in temperature, that is to say $dm_*(T_1)/dT_1$ is large enough. But this mass reduction is not reproducible with sufficient accuracy, and is thus not suitable for testing the measuring instrument. The mass changes very little after most of the volatile substances have evaporated, even if the temperature is raised, which results in a small gradient $dm_*(T_1)/dT_1$. Consequently, almost exactly the same mass is assigned to a wide temperature range, so that it is not possible to draw any conclusions about the accuracy of the measuring instrument. If the temperature is increased further after most of the volatile substances have evaporated, the mass changes more substantially again as a result of decomposition processes. However, the change in mass due to decomposition processes cannot be reproduced with sufficient accuracy and is therefore not suitable for use in testing the measuring instrument.

For these reasons, it is advantageous for testing the measuring instrument to ensure that the mass change $dm_*(T_1)/dT_1$ about the target temperature is sufficiently substantial, and also that this mass change, and thus also the final mass at the target temperature $m_1(T_1)$, is reproducible sufficiently accurately. Instead of the absolute value of the reference mass $m_*(T_1)$, the relative change in reference mass $X_*(T_1)$ or the relative change in mass after measurement operation $X(T_1)$ may also be considered. The relative change in reference mass $X_*(T_1)$ is defined on the basis of starting mass $m_0$ and the reference value of the mass $m_*(T_1)$:

$$X_*(T_1) = \frac{m_o - m_*(T_1)}{m_o}$$

The relative change in mass following the measurement operation $X(T_1)$ is defined on the basis of starting mass $m_0$ and the mass after the measurement operation $m_1$:

$$X(T_1) = \frac{m_o - m_1}{m_o}.$$

In order to be able to ensure that a $X_*(T_1)$ is able to be assigned uniquely to each target temperature $T_1$, the value of the derivative from the relative change in reference mass $X_*(T_1)$ after target temperature $T_1$ is greater than the quotient from relative mass tolerance $G_X$ of the weighing device and temperature tolerance $G_T$ of target temperature $T_1$.

The use of absolute values or relative values has no effect on the prerequisite for the material of the test sample.

For measuring instruments having a temperature tolerance of $G_T=3°$ C. and a relative mass tolerance of $G_X=0.1\%$, it follows that the amount of the derivative of the relative change in reference mass $X_*(T_1)$ after target temperature $T_1$ must be greater than $$\alpha = \frac{G_X}{G_T} \approx 0.033 \frac{\%}{°C}.$$

This condition must be fulfilled at least in a temperature range about target temperature $T_1$. It is normally sufficient if this condition is fulfilled for an interval of $\pm 10°$ C. about the value of target temperature $T_1$.

Ideally, the measuring instrument is tested with a target temperature $T_1$ that is as close as possible to the temperature at which the measuring instrument is operated. Measuring instruments of the type described earlier are normally operated in a target temperature range from $80°$ C. to $200°$ C. It is therefore advantageous to use a test sample that also behaves appropriately for this entire target temperature range. It is therefore advantageous if the amount of the derivative of the relative change in reference mass $X_*(T_1)$ is greater than the quotient from relative mass tolerance $G_X$ of the weighing device and temperature tolerance $G_T$ of the target temperature for all temperatures higher than $80°$ C. and lower than $200°$ C. For measuring instruments having a temperature tolerance of $G_T=3°$ C. and a relative mass tolerance of $G_X=0.1\%$ it is thus advantageous if the amount of the derivative of the relative change in reference mass $X_*(T_1)$ after target temperature $T_1$ is greater than $$\alpha = \frac{G_X}{G_T} = 0.033 \frac{\%}{°C}.$$

in the temperature range from $80°$ C. to $200°$ C.

This provides the advantage that the same test sample is able to be used for testing any target temperature from the interval $T_1 \in [80°$ C., $200°$ C.$]$.

The larger value $\alpha$ is, the more accurate the test procedure is. It is therefore advantageous if system components, and particularly the material of the test sample, are selected such that $\alpha > 0.1$ or preferably $\alpha > 0.3$ in a temperature range from $80°$ C. to $200°$ C.

The relative change in mass X, and thus also the relative change in final mass $X_1$, must be reproducible with sufficient accuracy. In order to evaluate the reproducibility, multiple measurements are performed. The measurements are carried out under identical conditions. The arithmetic mean $$\overline{X_1} = \frac{1}{n}\sum_{i=1}^{n} X_{1,i}$$

may be determined from the relative change in final mass $X_1$. In this context, n represents the number of measurements performed. The resulting standard deviation is calculated by $$s_X = \sqrt{\frac{1}{n-1}\sum_{i=1}^{n}(\overline{X_1} - X_{1,i})^2}.$$

The smaller $s_X$ is, the more accurate and thus more reproducible the method is. In order to ensure that temperature $T_1$ is in an interval of $T_1 - \Delta T$ to $T_1 + \Delta T$ with a probability of 95.4%, the following relationship must be fulfilled:

$$\frac{2 \cdot s_X}{\alpha} \leq \Delta T$$

The reproducibility of the method for testing the measuring instrument is good if $$\frac{2 \cdot s_X}{\alpha} \leq \Delta T = 5° \text{ C}.$$

If $$5° \text{ C}. < \frac{2 \cdot s_X}{\alpha} \leq \Delta T = 10° \text{ C}.$$

the method is still usable. However, if $$10° \text{ C}. < \frac{2 \cdot s_X}{\alpha},$$

the method cannot be reproduced sufficiently accurately, and the method cannot be used for testing the measuring instrument. The material of the test sample includes a test substance. Various substances and substance mixtures are suitable for use as the test substance, provided they undergo a controlled change in mass in response to the application of heat. Such a change in mass may take place as a result of a chemical or physical reaction in which, for example, the test substance decomposes, is converted, changes its aggregate state, or releases another bound or included substance such as water of crystallisation, gas inclusions, or absorbed solvents. Of course, volatile substances may also be used, provided they have a boiling point for example at least $20°$ C. above room temperature, to ensure that they may be stored without loss of mass. Starting mass $m_0$ of the test sample and target temperature $T_1$ are preferably selected such that a residual quantity of the test substance remains after predefined time interval $\Delta t$. If the test substance were to be completely converted or consumed before time interval $\Delta t$ elapsed, no further mass reduction could take place, and it would therefore be impossible to draw any conclusions regarding the accuracy of the measuring instrument.

Besides individual substances, it is of course possible to use mixtures of such substances as the test substance.

A test substance may be combined with a carrier material. The basic prerequisite for the carrier material is that it must have constant mass in a temperature range from $40°$ C. to $230°$ C. This carrier material is advantageously heat-resistant and does not undergo any change in the temperature range indicated previously.

A further advantageous property of the carrier material is even distribution of the test substance on the test seating, which has a positive effect on reproducible mass change in response to the application of heat.

Structures that are able to absorb and at least temporarily bind the test substance are particularly suitable for use as carrier materials. Such substances may include solids, gels, powders or granulates. Porous adsorbers or absorbers made from ceramic or textile compounds are particularly suitable. Particularly non-woven fabrics or microfibre products lend themselves particularly well for use as such textile compounds. Other possible carrier materials include zeolites, activated carbon, polymers, silica gels, quartz compounds, for example sand, or mixtures thereof, among others.

Zeolites are particularly advantageous because their microporous structure lends them a high capacity to absorb a suitable test substance, such as water, for example. The pore size of a zeolite is defined by its crystal structure, so that the pore size distribution is low. Zeolites are known to be able to bind water reversibly, which water is released continuously as the temperature increases. The water release by the zeolite is highly sensitive to temperature, resulting in a mass derivative according to mass dm/dT that is large relative to quantity. A further advantage of zeolites is they are both chemically and physically very stable, and also do not decompose in the temperature range under consideration. The form of most preferred carrier materials does not change in the temperature range used. However, it is also conceivable to use carrier materials whose structure or form is changed but without any change in mass, releasing the test substance, as a function of the temperature, for example before the target temperature is reached. In one possible variation, for example, a temperature-sensitive test substance is included in a meltable wax. In this way, the test substance is included in the wax while the test sample is stored, and cannot change or volatilise. When the test sample is heated during the test of the measuring instrument, the wax melts and the test substance is released. This variation offers advantages for storage of the test sample, since the temperature-sensitive test substance is not released until it is used to test the measuring instrument, not while it is being stored.

Liquids or solutions may be used as temperature-sensitive test substances, wherein the test substance may contain for example azeotropic mixtures, water, salt solutions, organic solvents, solvent mixtures and/or mixtures thereof. The temperature-sensitive substances have a well-defined boiling range. The temperature-sensitive test substance should be selected with consideration for its boiling point and the temperature or temperature range that is to be tested. The boiling point may be changed by using mixtures of substances having different boiling points than the test substance. The boiling point of the test substance may also be changed by adding other substances. Substances that undergo a chemical or physical change associated with a loss of weight in a range of 80° C. to 200° C. are particularly suitable as test substances.

It is advantageous to use the shortest possible period of time for testing the measuring instrument. On the other hand, however, the mass of the test sample must be large enough to yield a sufficiently accurate result. Experiments have shown that a predefined time interval in the range of $\Delta t=300$ s to $\Delta t=900$ s is sufficient for a staring mass of about 1 g to 20 g.

The starting mass of the test sample $m_0$ is constituted from the mass of the test substance $m_{test}$ and the mass of the carrier material $m_{Carrier}$:

$$m_0 = m_{test} + m_{Carrier}$$

In its original state, before measurement is begun, the test sample has a known initial state. In order to ensure that this is preserved, the packaging of the test sample must be selected such that this known original state remains sufficiently stable until the test of the measuring instrument is carried out. A test sample is normally only used for one test. It is usually not possible to reuse a test sample.

BRIEF DESCRIPTION OF THE DRAWINGS

An example of an instrument for gravimetric moisture measurement and typical temperature-mass profiles are shown in the following drawings, in which.

DETAILED DESCRIPTION OF THE DRAWINGS

Figure 1:
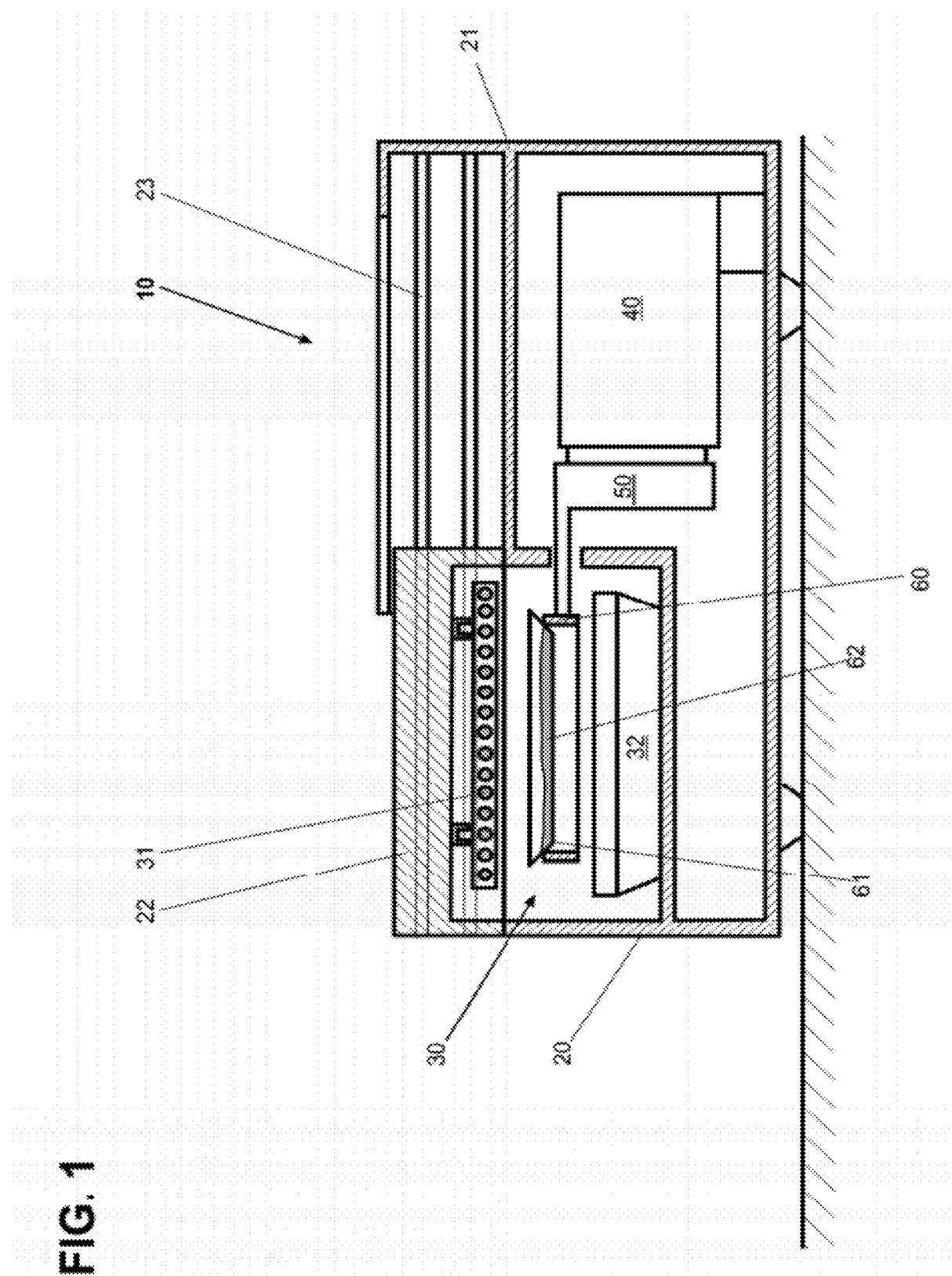
FIG. 1 is a sectional view of a measuring instrument for gravimetric moisture determination.

FIG. 1 shows a section through a typical measuring instrument 10 for gravimetric moisture determination having a sample holder 60 and a sample dish 61 for accommodating the sample. Sample holder 60 is connected to a weighing device 40 via a connecting member 50. Weighing device 40 is used to determine the mass of the sample.

Sample holder 60 is located in a test chamber 30 that is able to be heated by at least a first radiation source 31. Optionally, the sample may also be heated using a second radiation source 32. Ideally, first radiation source 31 is located above the sample and second radiation source 32 is located below the sample. When the sample is located between the two radiation sources 31, 32, this ensures that the sample will be heated evenly. Example of devices that may be used as radiation sources 31, 32 are a hot plate, a heating foil, and radiant heater, a ceramic heater, an induction coil, a halogen lamp or a quartz lamp.

Figures 2A, 2B:
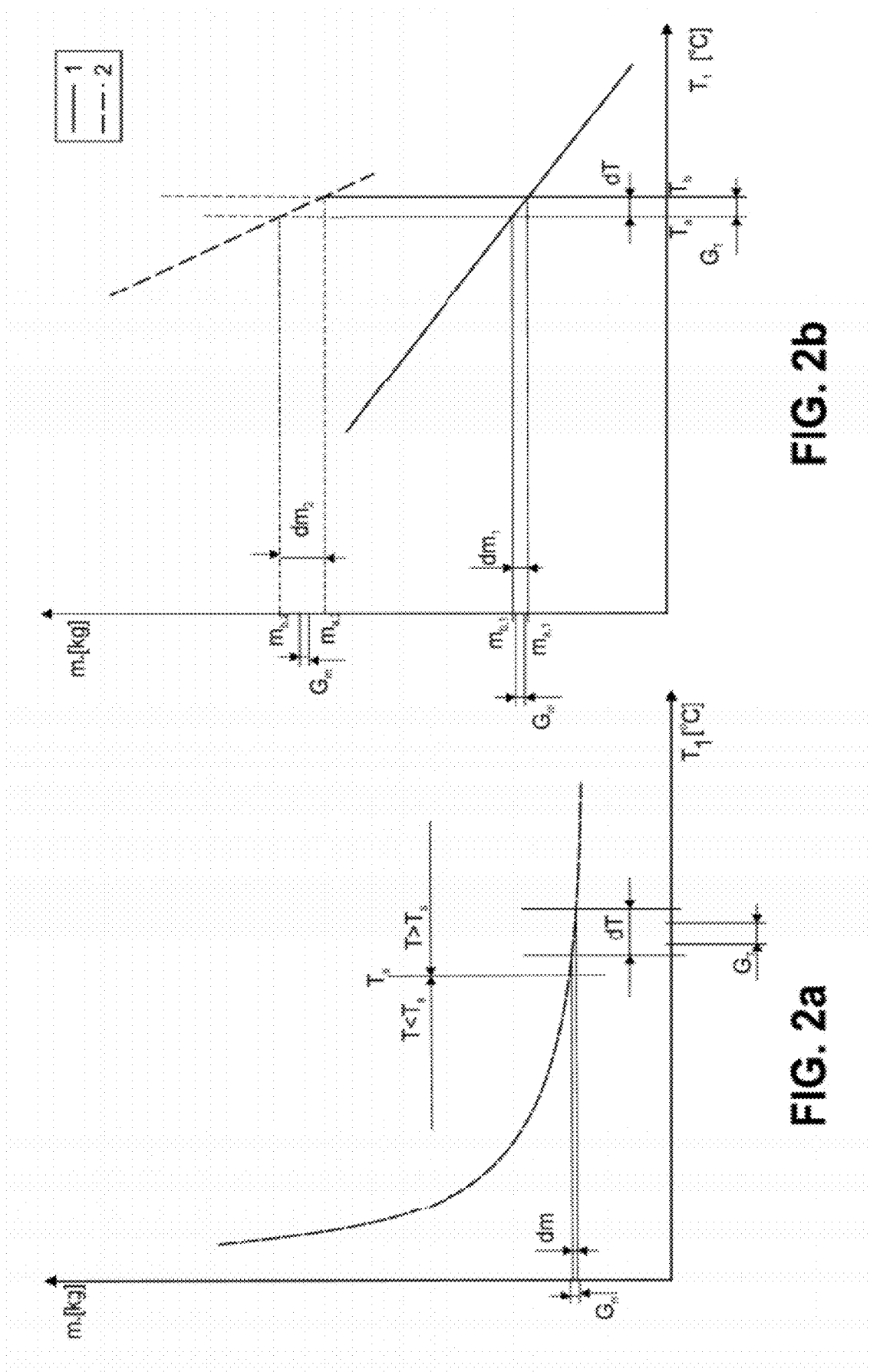
FIG. 2a shows a typical temperature-mass profile for sodium tartrate dihydrate, which is a test substance that is already known from the prior art.
FIG. 2b shows temperature-mass profiles for two test substances.

Measuring instrument 10 is accommodated in a housing 20. Housing 20 consists of a fixed 21 and a movable 22 housing part. Movable housing part 22 may be displaced on guide rails 23. Sliding movable housing part 22 causes test chamber 30 to open so that a sample 62 may be placed on sample holder 60 or removed therefrom. FIGS. 2a and 2b show temperature-mass profiles. In this context, target temperature $T_1$ is plotted along the horizontal axis, and the expected reference mass $m_*(T_1)$ resulting therefrom after a predefined constant time interval $\Delta t$ is plotted on the vertical axis. In theory, a higher target temperature $T_1$ results in a larger mass loss and thus a smaller reference mass $m_*(T_1)$.

FIG. 2a is a schematic representation of a typical temperature-mass profile for sodium tartrate dihydrate. Sodium tartrate dihydrate is a test substance that is known from the prior art.

The graph shows a slight increase at temperatures above temperature threshold value $T_S$. Even target temperatures that are farther apart than temperature tolerance $G_T$ result in masses lying within the mass tolerance $G_M$ for weighing device (40). Accordingly, no conclusions can be drawn regarding the accuracy of the measuring instrument.

Sodium tartrate dihydrate is also unsuitable for use below temperature threshold value $T_S$, because in this range, as was explained in the introduction, it is not possible to reproduce the mass-temperature profile with sufficient accuracy, so that is it also not suitable for a precise test of the measuring instrument.

FIG. 2b shows two graphs, each of different exemplary temperature-mass profiles for two different test substances. The two graphs differ in the steepness of the temperature-mass profile. The rise of the temperature-mass profile is reflected in the derivative of the mass after the temperature, dm/dT. The two graphs 1 and 2 show that if the derivative of the mass after the temperature is greater according to quantity than the quotient from temperature tolerance $G_T$ and mass tolerance $G_m$, that is to say $dm/dT > G_m/G_T$, a reference value for the mass, $m_{a,1}$ and $m_{b,1}$ may be assigned to each of two different target temperatures, $T_a$ and $T_b$, which differ from one another by at least temperature tolerance $G_T$. In this context, both masses $m_{a,1}$ and $m_{b,1}$ are farther apart than mass tolerance $G_m$. This ensures that the two masses $m_{a,1}$ and $m_{b,1}$ are not located within mass tolerance $G_m$ and accordingly it is possible to draw an accurate conclusion regarding the measuring instrument.

The steeper the gradient $dm/dT$, the more accurate the method is. This is demonstrated visually by comparing graphs 1 and 2. Graph 2 has a steep slope than graph 1. Accordingly, the reference values of the mass $m_{a,2}$ and $m_{b,2}$ are farther apart according for gradients $dm/dT$ that are larger according to quantity for two different target temperatures $T_a$ and $T_b$. As a result, the conclusion regarding the accuracy of the measuring instrument may be drawn more precisely.

Figures 3, 4:
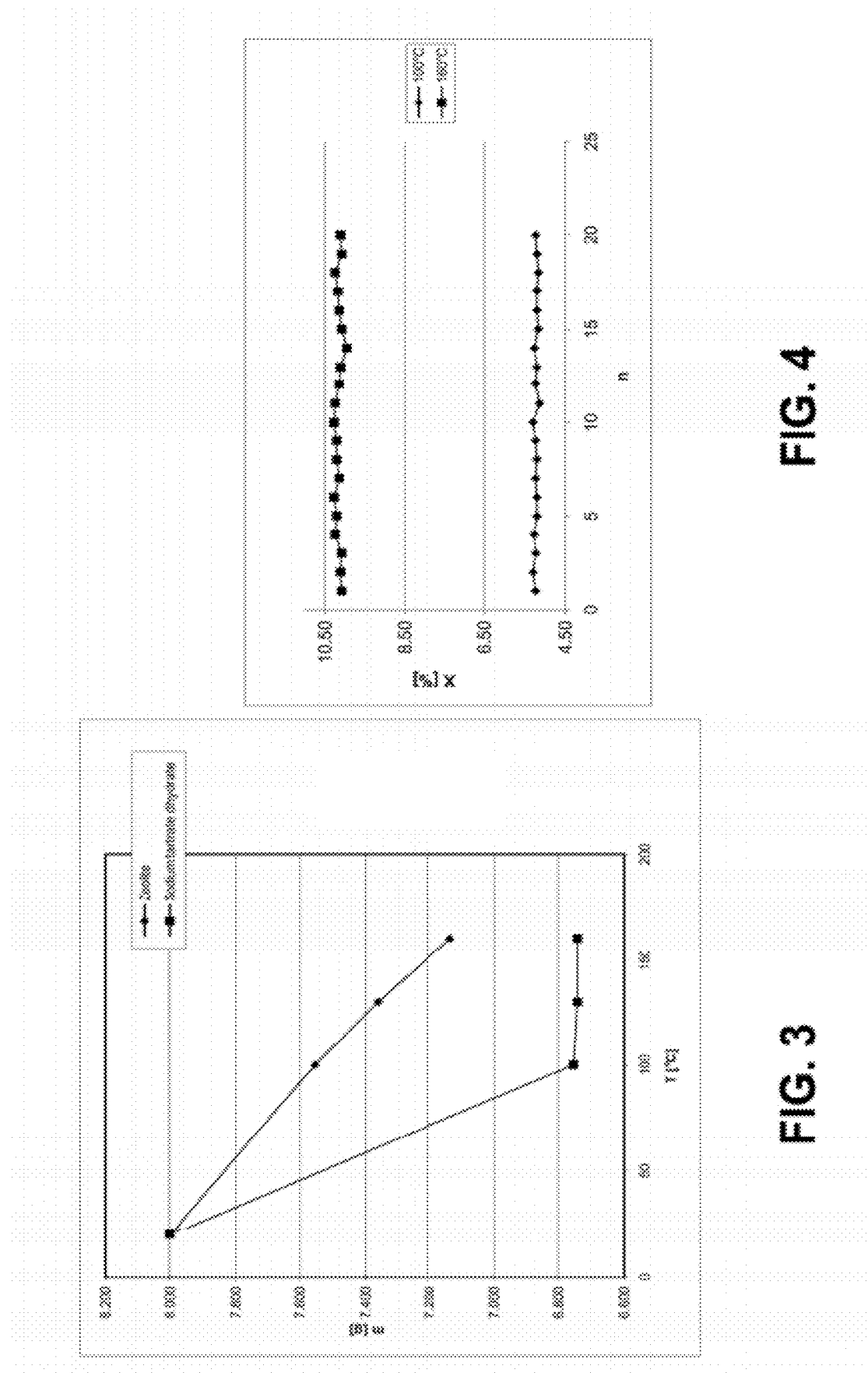
FIG. 3 shows the temperature-mass profile for a zeolite charged with water, together with sodium tartrate dehydrate.
FIG. 4 shows the measured mass after application of the method to a test sample containing a zeolite charged with water.

FIG. 3 shows the temperature-mass profile for a sodium tartrate dihydrate and for a zeolite charged with water. A temperature interval of 20° C. to 160° C. is considered A type 3A zeolite is used. This zeolite has a small pore size. Experiments have shown that it was possible to obtain good results in terms of accuracy and reproducibility of the measurement results with this zeolite.

A sample is placed in the moisture measuring instrument, each one either with zeolite or sodium tartrate dihydrate, and it is then heated. The mass of each sample, with the zeolite or with the sodium tartrate is 8 grams at the beginning of the method. Then, the sample is heated according to a predefined temperature profile. Heating the sample causes to lose some of its weight. The temperature-mass profile shown reveals that the mass of the sodium tartrate dihydrate falls sharply between 20° C. and 100° C. Above a temperature of 100° C., the mass of the sodium tartrate dihydrate hardly changes at all. These small changes in mass do not allow the temperature and mass to be correlated unambiguously. Accordingly, sodium tartrate dihydrate cannot be used in the method to test a moisture measuring instrument.

In contrast, in the case of zeolites the mass changes as a function of the temperature over the entire temperature interval under consideration. It is thus possible to correlate temperature and mass unambiguously.

FIG. 4 shows the relative change in final mass $X_1$ following application of the method to twenty test samples. The test samples uses contain zeolite 3A, which is charged water. At the start, the test sample weighs 8 gram, and is heated to $T_1=100°$ C. or $T_1=160°$ C. Temperature $T_1=100°$ C. or $T_1=160°$ C. is then maintained for ten minutes. Afterwards, the relative change in final mass $X_1$ is determined with the aid of a scale. The method was repeated twenty times for both $T_1=100°$ C. and $T_1=160°$ C. The relative changes in final mass $X_1$ are shown in FIG. 4. From the twenty $X_1$ the average of $$\overline{X_1} = \frac{1}{20} \sum_{i=1}^{20} X_{1,i} = 5.22\%$$

for $T_1 = 100°$ C. and $$\overline{X_1} = \frac{1}{20} \sum_{i=1}^{20} X_{1,i} = 10.15\%$$

for $T_1 = 160°$ C. were determined

In this context, n=20 represents the number of measurements performed. The standard deviation resulting from this is obtained by $$s_X = \sqrt{\frac{1}{20-1} \sum_{i=1}^{20} (\overline{X_1} - X_{1,i})^2} \approx 0.038\%$$

for $T_1 = 100°$ C. and $$s_X = \sqrt{\frac{1}{20-1} \sum_{i=1}^{20} (\overline{X_1} - X_{1,i})^2} \approx 0.079\%$$

for $T_1 = 160°$ C.

Measurements showed that $$\alpha = 0.09 \frac{\%}{°C}.$$

Accordingly:

$$\frac{2 \cdot s_X}{\alpha} = \frac{2 \cdot 0.038\%}{0.09 \frac{\%}{°C}} \approx 0.84° \text{ C.}$$

for $T_1 = 100°$ C. and $$\frac{2 \cdot s_X}{\alpha} = \frac{2 \cdot 0.079\%}{0.09 \frac{\%}{°C}} \approx 1.75° \text{ C.}$$

for $T_1=160°$ C. Thus, for both $T_1=100°$ C. and $T_1=160°$ C. it is follows that $$\frac{2 \cdot s_X}{\alpha} \leq \Delta T = 5° \text{ C.}$$

It was thus possible to show that the method for testing the moisture measuring instrument returns values that are readily reproducible.

Although the invention has been described with reference to specific embodiments, it is clear that many other variations of the embodiment may be created on the basis of the teaching of this invention, for example by combining the characterizing features of the individual embodiments with each other and/or substituting individual functional units.

In particular, the method according to the invention is not limited to the use of the measuring instrument described. It may be used with most commercially available instruments designed to measure moisture content gravimetrically.

What is claimed is:

1. A method, implemented on a computer, for testing a measuring instrument used for a gravimetric moisture determination of a sample, the measuring instrument having a test chamber, a weighing device with a sample holder for determining a mass of the sample that is located in the test chamber in a measuring position, and at least one means for heating the sample placed on the sample holder, the method comprising the steps of:

placing a test sample on the sample holder;
determining an initial mass of the test sample;

heating the test sample in the test chamber according to a predetermined temperature profile;

measuring, on the weighing device, a mass of the test sample resulting from the heating step;

comparing, in the computer, the measured mass to a predetermined reference value of the mass; and outputting a signal corresponding to the result of the comparison.

2. The method of claim 1, wherein:

the heating step comprises the substeps of:

heating to a predetermined target temperature; and maintaining the target temperature for one of: a predetermined time interval, or until the rate change in mass, based on time, is less than a predetermined fixed value.

3. The method of claim 2, wherein:

the test sample comprises a material selected to satisfy the condition that, in a temperature range about the target temperature, the derivative of the reference value of the mass with respect to temperature is greater after the target temperature than a ratio of a mass tolerance of the weighing device to a temperature tolerance of the target temperature.

4. The method of claim 2, wherein:

the test sample comprises a test substance having a mass that changes in a reproducible manner when heated.

5. The method of claim 4, wherein:

the test sample comprises a material selected to satisfy the condition that, in a temperature range about the target temperature, a rate change of the reference value of the mass, based on temperature, is greater after attaining the target temperature than a ratio of a mass tolerance of the weighing device to a temperature tolerance of the target temperature.

6. The method of claim 4, wherein:

the test sample comprises a material selected to satisfy the condition that a rate change of a normalized reference value of the mass, based on temperature, after attaining the target temperature is greater than a ratio of a mass tolerance of the weighing device to a temperature tolerance of the target temperature, where the normalized reference value of the mass is defined as the ratio of the difference between the initial and the reference values of the mass to the initial mass.

7. The method according to claim 6, wherein:

the test sample comprises a material selected such that, after the predetermined time interval, or when the rate change in mass, based on time, falls below the predetermined fixed value, the reference value of the mass depends upon the target temperature where, in a temperature range of 10° C. on either side of the target temperature, the rate change of the normalized reference value of the mass, based on temperature, is greater than 0.033% per ° C.

8. The method according to claim 6, wherein:

the normalized reference value of mass, after the target temperature, is greater than 0.1% per ° C. in a temperature range between 80 and 200° C.

9. The method of claim 8, wherein:

the normalized reference value of mass, after the target temperature, is greater than 0.3% per ° C. in a temperature range between 80 and 200° C.

10. The method of claim 1, wherein:

the test sample comprises a test substance that undergoes a chemical or physical change associated with a loss of weight in a range of from 80 to 200° C.

11. The method of claim 1, wherein:

the test sample comprises a test substance that is a liquid or a solution that is selected from the group consisting of: water, organic solvents, organic solvent mixtures and mixtures thereof.

12. The method of claim 1, wherein:

the test sample comprises a test substance whose mass changes as a result of at least a chemical reaction as a function of the temperature.

13. The method according to claim 1, wherein:

the test sample comprises a carrier material satisfying at least one of:

the carrier material has the form of a wax, a solid, a gel, a powder and a granulate; and the carrier material undergoes a change in form or structure but its mass remains unchanged as a function of the temperature.

14. The method according to claim 13, wherein:

the carrier material contains at least one of: a zeolite, an activated charcoal, a polymer, and a silica gel.

15. The method according to claim 13, wherein:

the carrier material is chemically and physically stable in the temperature range of from 40 to 230° C.

16. The method according to claim 15, wherein:

the carrier material contains at least one of: a zeolite, an activated charcoal, a polymer, and a silica gel.

17. The method of claim 1, wherein:

the corresponding signal is emitted on the basis of the difference between the reference value of the mass and the measured mass.

* * * * *